The present invention features methods and formulations or compositions for the treatment of colon cancer, and particularly for the inhibition, prevention and/or reduction of cancerous cell growth, as well as the destruction of early stage cancerous cells within the colon region of a mammal, wherein the formulations and compositions comprise an identified amount or concentration of a processed *Morinda citrifolia* product or an active ingredient there from, as obtained from the Indian Mulberry plant.

(12) United States Patent
Jensen et al.

(10) Patent No.: US 7,070,813 B2
(45) Date of Patent: Jul. 4, 2006

(54) PREVENTATIVE AND TREATMENT EFFECTS OF MORINDA CITRIFOLIA AS A COLON CANCER CELL GROWTH INHIBITOR

(75) Inventors: Claude Jarakae Jensen, Cedar Hills, UT (US); Afa Kehaati Palu, Orem, UT (US); Stephen P. Story, Alpine, UT (US); Summer Jensen, Cedar Hills, UT (US); Chen Su, West Jordan, UT (US)

(73) Assignee: Morinda, Inc., Provo, UT (US)

( * ) Notice: Subject to any disclaimer, the term of this patent is extended or adjusted under 35 U.S.C. 154(b) by 0 days.

(21) Appl. No.: 10/285,334

(22) Filed: Oct. 31, 2002

(65) Prior Publication Data

US 2003/0134001 A1 Jul. 17, 2003

Related U.S. Application Data

(60) Provisional application No. 60/335,346, filed on Nov. 2, 2001.

(51) Int. Cl.
*A61K 35/78* (2006.01)
(52) U.S. Cl. .................................................... 424/725
(58) Field of Classification Search ............. 424/195.1, 424/725
See application file for complete search history.

(56) References Cited

U.S. PATENT DOCUMENTS 5,595,756 A * 1/1997 Bally et al. .................. 424/450

OTHER PUBLICATIONS

Webb, D. Noni Juice Advice; Prevention magazine, Aug. 2000, vol. 52, p. 66, ProQuest [online] [retrieved on Jan. 30, 2004].*
Gura, T. Systems For Identifying New Drugs Are Often Faulty; Science, vol. 278, 1997, pp. 1041-1042.*

* cited by examiner

*Primary Examiner*—Patricia Leith
(74) *Attorney, Agent, or Firm*—Kirton & McConkie; Michael F. Krieger

(57) ABSTRACT

The present invention features methods and formulations or compositions for the treatment of colon cancer, and particularly for the inhibition, prevention and/or reduction of cancerous cell growth, as well as the destruction of early stage cancerous cells within the colon region of a mammal, wherein the formulations and compositions comprise an identified amount or concentration of a processed *Morinda citrifolia* product or an active ingredient there from, as obtained from the Indian Mulberry plant.

9 Claims, No Drawings

PREVENTATIVE AND TREATMENT EFFECTS OF MORINDA CITRIFOLIA AS A COLON CANCER CELL GROWTH INHIBITOR

RELATED APPLICATIONS

This application claims priority to U.S. Provisional Application Ser. No. 60/335,346, filed Nov. 2, 2001, entitled, "*Morinda citrifolia* Enhanced Colon Cancer Cell Growth Inhibitor".

BACKGROUND

1. Field of the Invention

The present invention relates to in vivo cell growth inhibitors, and more particularly to an in vivo cancer cell growth inhibitor formulated to inhibit colon cancer cell growth in mammals. Specifically, the present invention relates to an in vivo colon cancer cell growth inhibitor or naturaceutical composition formulated with *Morinda Citrifolia* from the Indian Mulberry plant.

2. Background of the Invention and Related Art

Cancer of the colon is a deadly form of cancer affecting millions of people. Research is ongoing in the fight against cancer, with hopes of one day finding a complete cure for this ugly disease. Until a complete cure is found, researchers, medical professionals, and several interested groups are furthering efforts to treat those currently suffering from the disease. As such, information and treatment possibilities are continuously being updated. The following represents the most current and up-to-date information pertaining to cancer of the colon.

Cancer of the colon is a disease in which malignant cells proliferate in the tissues of the colon, a vital organ of the digestive system of the body. As the purpose of the digestive system is to remove nutrients (vitamins, minerals, carbohydrates, fats, proteins, and water) from the foods eaten and to store the waste until it passes out of the body, the colon plays a critical role in the overall function of our body. The digestive system is made up of the esophagus, stomach, and the small and large intestines. The first 6 feet of intestine is called the large intestine or colon.

Several tests may be conducted to determine whether any abnormal genes or growths are present within the tissues of the colon. If tissue that is not normal is found, a small portion of the tissue may be removed to determine whether there are any cancerous cells present in the tissue.

If cancerous cells are discovered, the prognosis, or chance of recovery and choice of treatment depend on several factors, namely, the stage of the cancer (e.g. whether it is just in the inner lining of the colon or if it has spread to other places), and the patient's general state of health. After treatment, a blood test (to measure amounts of carcinoembryonic antigen or CEA in the blood) and x-rays may be done to see if the cancer is in remission.

The various stages of cancer serve to categorize the degree of growth of cancerous cells, as well as to determine whether the cancer has spread to other parts of the body. Knowing the stage of the disease will assist a physician in effectively planning further treatment.

There are currently three primary treatments available for patients with cancer of the colon. These treatments depend upon the stage of the cancer and the health of the individual seeking the treatment. Each one is briefly discussed.

First, cancerous cells may be surgically removed. This involves an expensive and dangerous process where the cancer is physically cut out and removed from the body. Surgery is the most common treatment of all stages of cancer of the colon. A doctor may surgically remove cancer from the colon using one of the following: if the cancer is found at a very early stage, the physician may laparoscopically excise the cancer. If the cancer is larger, the physician may excise the affected tissue and a small amount of healthy tissue around it (bowel or colon resection). The healthy parts of the colon are then sewn together (anastomosis). The physician will also take out lymph nodes near the intestine and look at them under the microscope to see if they contain cancer. If the physician is not able to sew the colon back together, he or she will make an opening (stoma) on the outside of the body for waste to pass out of the body. This is called a colostomy. Sometimes, the colostomy is only needed until the colon has healed, and then it can be reversed. However, the doctor may have to take out the entire lower colon and the colostomy is permanent. If a patient has a colostomy, a special bag will need to be worn to collect body wastes. This special bag, which sticks to the skin around the stoma with a special glue, can be thrown away after it is used. This bag does not show under clothing, and most people take care of these bags themselves.

The next form of treatment is radiation therapy. Radiation therapy involves using high-dose x-rays or other high energy radiation to kill the cancer cells. Radiation therapy is the use of x-rays or other high-energy rays to kill cancer cells and shrink tumors. Radiation may come from a machine outside the body (external radiation therapy) or from putting materials that contain radiation through thin plastic tubes (internal radiation therapy) in the intestine area. Radiation can be used alone or in addition to surgery and/or chemotherapy.

Chemotherapy is another possible treatment. This procedure uses drugs to kill cancerous cells. Chemotherapy may be administered through capsules, or intravenously. A patient may be given chemotherapy through a catheter while a small pump gives the patient constant treatment over a period of weeks. Chemotherapy is a systemic treatment because the drug enters the bloodstream, travels through the body, and can kill cancer cells outside the colon. If the cancer has spread to the liver, the patient may be given chemotherapy directly into the artery going to the liver. If the doctor removes all of the cancer that can be seen at the time of the operation, the patient may be given chemotherapy after surgery to kill any cancer cells that are left. Chemotherapy given after an operation to a person who has no cancer cells that can be seen is called adjuvant chemotherapy.

The following five stages are used to determine the progression of cancer of the colon.

Stage 0 cancer of the colon, or carcinoma in situ, is very early cancer. The cancer is found only in the innermost lining of the colon. Treating stage 0 colon cancer may involve local excision or simple polypectomy to remove all the cancer, or surgery (bowel resection).

Stage I cancer of the colon, or Dukes A colon cancer, is more progressive in that the cancer has spread beyond the innermost lining of the colon to the second and third layers and involves the inside wall of the colon, but has not spread to the outer wall of the colon or outside the colon. Treating stage I colon cancer usually involves surgery (bowel resection) to remove the cancer and join the cut ends of the bowel.

Stage II cancer of the colon, or Dukes B colon cancer, is cancer that has spread outside the colon to nearby tissue, but has not yet gone into the lymph nodes—small, bean-shaped structures found throughout the body that produce and store cells that fight infection. Treating stage II colon cancer may involve surgery (bowel resection) to remove the cancer, clinical trials of chemotherapy, radiation therapy, or biological therapy following surgery, or if the tumor has spread to nearby tissue, a patient may also receive chemotherapy and/or radiation therapy following surgery.

Stage III cancer of the colon, or Dukes C colon cancer, is cancer that has spread to nearby lymph nodes, but not yet to other parts of the body. Treating stage II colon cancer usually involves surgery (bowel resection) to remove the cancer, followed by chemotherapy. In addition, clinical trials of chemotherapy, radiation therapy, and/or biological therapy following surgery may also be employed.

Stage IV cancer of the colon, or Dukes D colon cancer, is cancer that has spread to other parts of the body. This is the most severe of the stages. Treating stage IV colon cancer may involve surgery to remove the cancer or to make the colon go around the cancer so that it can still work; surgery to remove parts of other organs such as the liver, lungs, and ovaries, where the cancer may have spread; chemotherapy to relieve symptoms; clinical trials of chemotherapy or biological therapy; and radiation therapy to relieve symptoms.

While these efforts alleviate, and in some instances remove, the threat of colon cancer in an individual, these treatments can be extremely costly and unpredictable. Moreover, these treatments can be dangerous, not to mention putting incredible amounts of physical strain upon the individual.

SUMMARY AND OBJECTS OF THE INVENTION

The present invention is directed to methods of inhibiting growth of cancerous cells in the colon and colon region of mammals by introducing into the body (e.g. ingesting) a safe, pre-determined dosage of a naturaceutical composition formulated with or comprising one or more processed *Morinda citrifolia* products.

In one currently preferred embodiment, a quantity of *Morinda citrifolia* fruit juice, puree juice or juice puree, pulp, seed oil, and/or dietary fiber is obtained, using the process as described below. Subsequently, an amount of any one of or a combination of these is formulated with other ingredients to create a naturaceutical composition formulated to provide significant health advantages and to assist in the treatment of and inhibition of cancer cell growth within the colon.

To achieve the foregoing objects, and in accordance with the invention as embodied and broadly described herein, the present invention features a naturaceutical composition formulated with *Morinda citrifolia* for the inhibition of cancer cell growth within the colon; and a method of administering the same.

The present invention naturaceutical composition comprises *Morinda citrifolia* in one of its several forms (preferably the fruit juice), formulated with other ingredients, either natural or artificial, as needed. The preferred naturaceutical composition is a liquid that may be administered orally or through intravenous injection, wherein the active ingredients, namely *Morinda citrifolia*, are allowed to be absorbed into the tissues of the colon to inhibit the growth of cancerous cells within the colon.

The present invention further features a method of inhibiting cancer cell growth through the prophylactic administration of a naturaceutical composition comprising *Morinda citrifolia* as an active ingredient.

The present invention further features a method for introducing an internal composition to an infected area of the colon, wherein the internal composition comprises one or more processed *Morinda citrifolia* products.

DETAILED DESCRIPTION OF THE PREFERRED EMBODIMENTS

It will be readily understood that the components of the present invention, as generally described herein, could be arranged and designed in a wide variety of different configurations. Thus, the following more detailed description of the embodiments of the system and method of the present invention is not intended to limit the scope of the invention, as claimed, but is merely representative of the presently preferred embodiments of the invention.

The present invention describes and features a method and formulation for inhibiting cancerous cell growth in the colon of a mammal, and particularly to the inhibition, blocking, and/or prevention of cancerous cell growth within the colon region of a mammal, as well as a method and formulation for destroying pre-existing cancerous cells within the colon, each through the prophylactic administration of a naturaceutical formulation comprising *Morinda citrifolia* in processed form.

The presently preferred embodiments of the invention will be best understood, and is benefits and advantages more clearly pointed out, by separating the description into sections, the first pertaining to a general discussion regarding *Morinda citrifolia*, including its origins, processing techniques, and health benefits, and the methods employed to produce and manufacture the processed *Morinda citrifolia* products used as key ingredients in the naturaceutical formulations described herein; and the second being a more detailed and specific discussion on the formulations, compositions, and methods comprising the processed *Morinda citrifolia* product as described herein that are used to treat colon cancer and its symptoms, and specifically used to inhibit the growth, proliferation, metastasizing, and vitality of cancerous cells within the region of the colon. Examples of experimental studies and the results obtained are also provided herein.

General Discussion of *Morinda citrifolia* and the Methods Used to Produce Processed *Morinda citrifolia* Products The Indian Mulberry or Noni plant, known scientifically as *Morinda Citrifolia* L. (*Morinda citrifolia*), is a shrub or small tree up to 10 m in height. The leaves are oppositely arranged with an elliptic to ovate form. The small white flowers are contained in a fleshy, globose, head-like cluster. The fruits are large, fleshy, and ovoid. At maturity, they are creamy-white and edible, but have an unpleasant taste and odor. The plant is native to Southeast Asia and has spread in early times to a vast area from India to eastern Polynesia. It grows randomly in the wild, and it has been cultivated in plantations and small individual growing plots. The *Morinda citrifolia* flowers are small, white, three to five lobed, tubular, fragrant, and about 1.25 cm long. The flowers develop into compound fruits composed of many small drupes fused into an ovoid, ellipsoid or roundish, lumpy body, with waxy, white, or greenish-white or yellowish, semi-translucent skin. The fruit contains "eyes" on its surface, similar to a potato. The fruit is juicy, bitter, dull-yellow or yellowish-white, and contains numerous red-brown, hard, oblong-triangular, winged 2-celled stones, each containing four seeds.

When fully ripe, the fruit has a pronounced odor like rancid cheese. Although the fruit has been eaten by several nationalities as food, the most common use of the *Morinda citrifolia* plant was as a red and yellow dye source. Recently, there has been an interest in the nutritional and health benefits of the *Morinda citrifolia* plant, further discussed below.

Because the *Morinda citrifolia* fruit is for all practical purposes inedible, the fruit must be processed in order to make it palatable for human consumption and included in the naturaceutical used to treat colon cancer. Processed *Morinda citrifolia* fruit juice can be prepared by separating seeds and peels from the juice and pulp of a ripened *Morinda citrifolia* fruit; filtering the pulp from the juice; and packaging the juice. Alternatively, rather than packaging the juice, the juice can be immediately included as an ingredient in another food product, frozen or pasteurized. In some embodiments, the juice and pulp can be pureed into a homogeneous blend to be mixed with other ingredients. Other process include freeze drying the fruit and juice. The fruit and juice can be reconstituted during production of the final juice product. Still other processes include air drying the fruit and juices, prior to being masticated.

The present invention also contemplates the use of fruit juice and/or puree fruit juice extracted from the *Morinda Citrifolia* plant. In a currently preferred process of producing *Morinda citrifolia* fruit juice, the fruit is either hand picked or picked by mechanical equipment. The fruit can be harvested when it is at least one inch (2–3 cm) and up to 12 inches (24–36 cm) in diameter. The fruit preferably has a color ranging from a dark green through a yellow-green up to a white color, and gradations of color in between. The fruit is thoroughly cleaned after harvesting and before any processing occurs.

The fruit is allowed to ripen or age from 0 to 14 days, with most fruit being held from 2 to 3 days. The fruit is ripened or aged by being placed on equipment so it does not contact the ground. It is preferably covered with a cloth or netting material during aging, but can be aged without being covered. When ready for further processing the fruit is light in color, from a light green, light yellow, white or translucent color. The fruit is inspected for spoilage or for excessively green color and hard firmness. Spoiled and hard green fruit is separated from the acceptable fruit.

The ripened and aged fruit is preferably placed in plastic lined containers for further processing and transport. The containers of aged fruit can be held from 0 to 30 days. Most fruit containers are held for 7 to 14 days before processing. The containers can optionally be stored under refrigerated conditions prior to further processing. The fruit is unpacked from the storage containers and is processed through a manual or mechanical separator. The seeds and peel are separated from the juice and pulp.

The juice and pulp can be packaged into containers for storage and transport. Alternatively, the juice and pulp can be immediately processed into a finished juice product. The containers can be stored in refrigerated, frozen, or room temperature conditions.

The *Morinda citrifolia* juice and pulp are preferably blended in a homogenous blend, after which they may be mixed with other ingredients, such as flavorings, sweeteners, nutritional ingredients, botanicals, and colorings. The finished juice product is preferably heated and pasteurized at a minimum temperature of 181° F. (83° C.) or higher up to 212° F. (100° C.).

Another product manufactured is *Morinda citrifolia* puree and puree juice, in either concentrate or diluted form. Puree is essentially the pulp a separated from the seeds and is different than the fruit juice product described herein.

Each product is filled and sealed into a final container of plastic, glass, or another suitable material that can withstand the processing temperatures. The containers are maintained at the filling temperature or may be cooled rapidly and then placed in a shipping container. The shipping containers are preferably wrapped with a material and in a manner to maintain or control the temperature of the product in the final containers.

The juice and pulp may be further processed by separating the pulp from the juice through filtering equipment. The filtering equipment preferably consists of, but is not limited to, a centrifuge decanter, a screen filter with a size from 1 micron up to 2000 microns, more preferably less than 500 microns, a filter press, reverse osmosis filtration., and any other standard commercial filtration devices. The operating filter pressure preferably ranges from 0.1 psig up to about 1000 psig. The flow rate preferably ranges from 0.1 g.p.m. up to 1000 g.p.m., and more preferably between 5 and 50 g.p.m. The wet pulp is washed and filtered at least once and up to 10 times to remove any juice from the pulp. The wet pulp typically has a fiber content of 10 to 40 percent by weight. The wet pulp is preferably pasteurized at a temperature of 181° F. (83° C.) minimum and then packed in drums for further processing or made into a high fiber product.

The processed *Morinda citrifolia* product may also exist as a dietary fiber. Still further, the processed *Morinda citrifolia* product may also exist in oil form. The *Morinda citrifolia* oil typically includes a mixture of several different fatty acids as triglycerides, such as palmitic, stearic, oleic, and linoleic fatty acids, and other fatty acids present in lesser quantities. In addition, the oil preferably includes an antioxidant to inhibit spoilage of the oil. Conventional food grade antioxidants are preferably used.

The *Morinda citrifolia* plant is rich in natural ingredients. Those ingredients that have been discovered include: (from the leaves): alanine, anthraquinones, arginine, ascorbic acid, aspartic acid, calcium, beta-carotene, cysteine, cystine, glycine, glutamic acid, glycosides, histidine, iron, leucine, isoleucine, methionine, niacin, phenylalanine, phosphorus, proline, resins, riboflavin, serine, beta-sitosterol, thiamine, threonine, tryptophan, tyrosine, ursolic acid, and valine; (from the flowers): acacetin-7-o-beta-d(+)-glucopyranoside, 5,7-dimethyl-apigenin-4'-o-beta-d(+)-galactopyranoside, and 6,8-dimethoxy-3-methylanthraquinone-1-o-beta-rhamnosyl-glucopyranoside; (from the fruit): acetic acid, asperuloside, butanoic acid, benzoic acid, benzyl alcohol, 1-butanol, caprylic acid, decanoic acid, (E)-6-dodeceno-gamma-lactone, (Z,Z,Z)-8,11,14-eicosatrienoic acid, elaidic acid, ethyl decanoate, ethyl hexanoate, ethyl octanoate, ethyl palmitate, (Z)-6-(ethylthiomethyl) benzene, eugenol, glucose, heptanoic acid, 2-heptanone, hexanal, hexanamide, hexanedioic acid, hexanoic acid (hexoic acid), 1-hexanol, 3-hydroxy-2-butanone, lauric acid, limonene, linoleic acid, 2-methylbutanoic acid, 3-methyl-2-buten-1-ol, 3-methyl-3-buten-1-ol, methyl decanoate, methyl elaidate, methyl hexanoate, methyl 3-methylthio-propanoate, methyl octanoate, methyl oleate, methyl palmitate, 2-methylpropanoic acid, 3-methylthiopropanoic acid, myristic acid, nonanoic acid, octanoic acid (octoic acid), oleic acid, palmitic acid, potassium, scopoletin, undecanoic acid, (Z,Z)-2,5-undecadien-1-ol, and vomifol; (from the roots): anthraquinones, asperuloside (rubichloric acid), damnacanthal, glycosides, morindadiol, morindine, morindone, mucilaginous matter, nor-damnacanthal, rubiadin, rubiadin monomethyl ether, resins, soranjidiol, sterols, and trihydroxymethyl anthraquinone-monomethyl ether; (from the root bark): alizarin, chlororubin, glycosides (pentose, hexose), morindadiol, morindanigrine, morindine, morindone, resinous matter, rubiadin monomethyl ether, and soranjidiol; (from the wood): anthragallol-2,3-dimethylether; (from the tissue culture): damnacanthal, lucidin, lucidin-3-primeveroside, and morindone-6beta-primeveroside; (from the plant): alizarin, alizarin-alpha-methyl ether, anthraquinones, asperuloside, hexanoic acid, morindadiol, morindone, morindogenin, octanoic acid, and ursolic acid.

Recently, as mentioned, many health benefits have been discovered stemming from the use of products containing *Morinda citrifolia*. One benefit of *Morinda citrifolia* is found in its ability to isolate and produce Xeronine, which is a relatively small alkaloid physiologically active within the body. Xeronine occurs in practically all healthy cells of plants, animals and microorganisms. Even though *Morinda citrifolia* has a negligible amount of free Xeronine, it contains appreciable amounts of the precursor of Xeronine, called Proxeronine. Further, *Morinda citrifolia* contains the inactive form of the enzyme Proxeronase which releases Xeronine from Proxeronine. A paper entitled, "The Pharmacologically Active Ingredient of Noni" by R. M. Heinicke of the University of Hawaii, indicates that *Morinda citrifolia* is "the best raw material to use for the isolation of xeronine," because of the building blocks of Proxeronine and Proxeronase. These building blocks aid in the isolation and production of Xeronine within the body. The function of the essential nutrient Xeronine is fourfold.

First, Xeronine serves to activate dormant enzymes found in the small intestines. These enzymes are critical to efficient digestion, calm nerves, and overall physical and emotional energy.

Second, Xeronine protects and keeps the shape and suppleness of protein molecules so that they may be able to pass through the cell walls and be used to form healthy tissue. Without these nutrients going into the cell, the cell cannot perform its job efficiently. Without Proxeronine to produce Xeronine our cells, and subsequently the body, suffer.

Third, Xeronine assists in enlarging the membrane pores of the cells. This enlargement allows for larger chains of peptides (amino acids or proteins) to be admitted into the cell. If these chains are not used they become waste.

Fourth, Xeronine, which is made from Proxeronine, assists in enlarging the pores to allow better absorption of nutrients.

Each tissue has cells which contain proteins which have receptor sites for the absorption of Xeronine. Certain of these proteins are the inert forms of enzymes which require absorbed Xeronine to become active. Thus Xeronine, by converting the body's procollagenase system into a specific protease, quickly and safely removes the dead tissue from skin. Other proteins become potential receptor sites for hormones after they react with Xeronine. Thus the action of *Morinda citrifolia* in making a person feel well is probably caused by Xeronine converting certain brain receptor proteins into active sites for the absorption of the endorphin, the well being hormones. Other proteins form pores through membranes in the intestines, the blood vessels and other body organs. Absorbing Xeronine on these proteins changes the shape of the pores and thus affects the passage of molecules through the membranes.

Because of its many benefits, *Morinda citrifolia* has been known to provide a number of anecdotal effects in individuals having cancer, arthritis, headaches, indigestion, malignancies, broken bones, high blood pressure, diabetes, pain, infection, asthma, toothaches, blemishes, immune system failure, and others.

The compositions containing *Morinda citrifolia* may be in a form suitable for oral use, for example, as tablets, or lozenges, aqueous or oily suspensions, dispersible powders or granules, emulsions, syrups or elixirs. Compositions intended for oral use may be prepared according to any method known in the art for the manufacture of *Morinda citrifolia* compositions and such compositions may contain one or more agents selected from the group consisting of sweetening agents, flavoring agents, coloring agents and preserving agents. Tablets contain *Morinda citrifolia* in admixture with non-toxic pharmaceutically acceptable excipients which are suitable for the manufacture of tablets. These excipients may be for example, inert diluents, granulating and disintegrating agents, binding agents, and lubricating agents. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Aqueous suspensions contain the *Morinda citrifolia* in admixture with excipients suitable for the manufacture of aqueous suspensions. Such excipients are suspending, agents, for example, sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitor monooleate, or condensation products of ethylene oxide with partial esters derived from fatty acids and hexitol anhydrides, for example polyethylene sorbitan monooleate.

Favorably, this invention provides a method of treating colon cancer with a *Morinda citrifolia*-based naturaceutical formulation without any significant tendency to cause gastric side effects.

*Morinda Citrifolia*-Based Naturaceutical
Formulations and Methods of Administration for
Inhibiting Cancer Cell Growth Within the Region
of the Colon The present invention advances cancer cell growth inhibitors by providing a naturaceutical composition or colon cancer cell growth inhibitor or treatment formulated with *Morinda citrifolia* from the Indian Mulberry plant. The *Morinda citrifolia* is incorporated into various carriers or naturaceutical compositions suitable for in vivo treatment of a patient. For instance, the inhibitor may be ingested, introduced through an intravenous injection or feeding, or otherwise internalized as is appropriate and directed.

In one exemplary embodiment, the naturaceutical composition of the present invention comprises one or more of a processed *Morinda citrifolia* product present in an amount by weight between about 0.01 and 100 percent by weight, and preferably between 0.01 and 95 percent by weight. Several embodiment of formulations are provided below. However, these are only intended to be exemplary as one ordinarily skilled in the art will recognize other formulations or compositions comprising the processed *Morinda citrifolia* product.

The processed *Morinda citrifolia* product is the active ingredient or contains one or more active ingredients, such as Quercetin and Rutin, and others, for effectuating the inhibition and prevention of growth of the cancerous cells within the colon, as well as for effectuating the destruction of cancerous cells, and particularly early stage cancerous cells. Active ingredients may be extracted out using various alcohol or alcohol-based solutions, such as methanol, ethanol, and ethyl acetate, and other alcohol-based derivatives using any known process in the art. The active ingredients of Quercetin and Rutin are present in amounts by weight ranging from 0.01–10 percent of the total formulation or composition. These amounts may be concentrated as well into a more potent concentration in which they are present in amounts ranging from 10 to 100 percent.

The processed *Morinda citrifolia* product may be formulated with various other ingredients to produce various compositions, such as a naturaceutical composition, an internal composition, or others. The ingredients to be utilized in a naturaceutical composition are any that are safe for introduction into the body of a mammal, and particularly a human, and may exist in various forms, such as liquids, tablets, lozenges, aqueous or oily solutions, dispersible powders or granules, emulsions, syrups, elixirs, etc. Moreover, since the naturaceutical composition will most likely be consumed orally, it may contain one or more agents selected from the group consisting of sweetening agents, flavoring agents, coloring agents, preserving agents, and other medicinal agents as directed.

The ingredients to be utilized in a topical dermal composition are also any that are safe for internalizing into the body of a mammal and may exist in various forms, such as gels, lotions, creams, ointments, etc., each comprising one or more carrier agents. The ingredients for systemically administered formulations may also comprise any known in the art.

In one exemplary embodiment, the present invention further features a method of administering a naturaceutical composition to a mammal for the treatment of colon cancer. The method comprises the steps of (a) formulating a naturaceutical composition comprising in part a processed *Morinda citrifolia* product present in an amount between about 0.01 and 95 percent by weight, wherein the composition also comprises a carrier, such as water or purified water, and other natural or artificial ingredients; (b) administering the naturaceutical composition into the body such that the processed *Morinda citrifolia* product is sufficiently internalized and concentrated within the colon; (c) repeating the above steps as often as necessary to provide an effective amount of the processed *Morinda citrifolia* product to the tissues of the colon.

The step of administering the naturaceutical composition into the body comprises ingesting the composition orally through one of several means. Specifically, the naturaceutical composition may be formulated as a liquid, gel, solid, or some other type that would allow the composition to be quickly digested and concentrated within the colon. It is important to note that the step of administering the naturaceutical composition should be carried out in an effective manner so that the greatest concentration of naturaceutical composition is allowed to reach the colon. For the naturaceutical composition to take effect, it must be sufficiently internalized into the tissue of the colon. Once sufficiently internalized, it may then begin to act upon the abnormal cancerous cells by inhibiting their growth.

In addition, the step of administering the naturaceutical composition may include injecting the composition into the body using an intravenous pump. This technique is advantageous as it would allow the composition to be localized in the area where it would have the most effect, or the area that would provide for the greatest concentration of the naturaceutical composition within the colon.

In one exemplary embodiment, the naturaceutical composition is administered by taking between 1 teaspoon and 2 oz., and preferably 2 oz., of the naturaceutical composition every two hours each day, or at least twice a day. Also, the naturaceutical composition is to be taken on an empty stomach, meaning at a period of time at least two hours prior to consumption of any food or drink. Following this, the naturaceutical composition is allowed to actively impact the cancerous cells within the colon, thereby inhibiting their growth and combating the effects of the cancer. Of course, one ordinarily skilled in the art will recognize that the amount of composition and frequency of use may vary from individual to individual.

The following tables illustrate or represent some of the preferred formulations or compositions contemplated by the present invention. As stated, these are only intended as exemplary embodiments and are not to be construed as limiting in any way.

| Ingredients | Percent by Weight |
| --- | --- |
| Formulation One | |
| *Morinda citrifolia* puree juice or fruit juice | 100% |
| Formulation Two | |
| *Morinda citrifolia* fruit juice | 85–99.99% |
| water | 0.1–15% |
| Formulation Three | |
| *Morinda citrifolia* fruit juice | 85–99.99% |
| non-*Morinda citrifolia*-based fruit juices | 0.1–15% |
| Formulation Four | |
| *Morinda citrifolia* fruit juice | 50–90% |
| water | 0.1–50% |
| non-*Morinda citrifolia*-based fruit juices | 0.1–30% |
| Formulation Five | |
| *Morinda citrifolia* puree juice | 85–99.9% |
| water | 0.1–15% |
| Formulation Six | |
| *Morinda citrifolia* puree juice | 85–99.9% |
| non-*Morinda citrifolia*-based fruit juices | 0.1–15% |
| Formulation Seven | |
| *Morinda citrifolia* puree juice | 50–90% |
| water | 0.1–50% |
| non-*Morinda citrifolia*-based fruit juices | 0.1–30% |
| Formulation Eight | |
| *Morinda citrifolia* dietary fiber | 0.1–30% |
| water | 1–99.9% |
| non-*Morinda citrifolia*-based fruit juices | 1–99.9% |
| Formulation Nine | |
| *Morinda citrifolia* dietary fiber | 0.1–30% |
| water | 1–99.9% |
| *Morinda citrifolia* fruit juice or puree juice | 1–99.9% |
| Formulation Ten | |
| *Morinda citrifolia* oil | 0.1–30% |
| carrier medium | 70–99.9% |
| other ingredients | 1–95% |

-continued

| Ingredients | Percent by Weight |
|---|---|
| Formulation Eleven | |
| *Morinda citrifolia* product | 10–80% |
| carrier medium | 20–90% |
| Formulation Twelve | |
| *Morinda citrifolia* product | 5–80% |
| carrier medium | 20–95% |
| Formulation Thirteen | |
| *Morinda citrifolia* oil or oil extract | 0.1–20% |
| carrier medium | 20–90% |
| Formulation Fourteen | |
| *Morinda citrifolia* puree juice or fruit Juice | 0.1–80% |
| *Morinda citrifolia* oil | 0.1–20% |
| carrier medium | 20–90% |
| Formulation Fifteen | |
| *Morinda citrifolia* puree juice concentrate or fruit juice concentrate | 100% |
| Formulation Sixteen | |
| *Morinda citrifolia* fruit juice concentrate or puree juice concentrate | 85–99.99% |
| water | 0.1–15% |

In one preferred method, a person suffering from colon cancer as described above takes, or is administered, at least one (1) ounce of Formulation One in the morning on an empty stomach, and at least one (1) ounce at night on an empty stomach, just prior to retiring to bed. In one example, which is not meant to be limiting in any way, the beneficial *Morinda Citrifolia* is processed into Tahitian Noni® juice manufactured by Morinda, Incorporated of Orem, Utah.

As stated, in one exemplary embodiment, the present invention features a method for introducing an internal composition of formulation to a region in the colon infected or afflicted with cancerous cells. This method essentially comprises the introduction of an internal composition to the colon region infected with the cancerous cells. Several embodiments of the internal comprising various different ingredients are contemplated for use herein, with each embodiment comprising one or more forms of a processed *Morinda citrifolia* product as taught and explained herein and a carrier agent or medium.

In one exemplary embodiment, the internal composition comprises the ingredients of: a processed *Morinda citrifolia* product present in an amount by weight between about 10–80 percent; and a carrier medium present in an amount by weight between about 20–90 percent.

In this embodiment, the processed *Morinda citrifolia* product may comprise one or more of processed *Morinda citrifolia* fruit juice, processed *Morinda citrifolia* puree juice, processed *Morinda citrifolia* dietary fiber, and/or processed *Morinda citrifolia* oil extract.

In another exemplary embodiment, the internal composition comprises the ingredients of: processed *Morinda citrifolia* fruit juice or puree juice present in an amount by weight between about 0.1–80 percent; processed *Morinda citrifolia* oil present in an amount by weight between about 0.1–20 percent; and a carrier medium present in an amount by weight between about 20–90 percent. *Morinda citrifolia* puree juice or fruit juice may also be formulated with a *Morinda citrifolia* dietary fiber product in similar concentrations.

According to the present invention, these particular methods of introducing an internal composition may comprises any method of actually introducing the internal composition to the colon and/or the colon region of the patient that is infected with cancer or cancerous cells. Although the particular methods are many, the present invention recognizes that the internal composition may be introduced intravenously, transdermally, orally, or systemically. No matter what method is employed, it is important to thoroughly expose the cancer infected area of the colon to the internal composition so that the internal composition can effectively treat the cancer and subsequent inhibition and prevention of the growth of the cancerous cells may be abated, and also so that any early stage cancerous cells can be destroyed.

The carrier medium may comprise any ingredient capable of being introduced into the body of a mammal, and that is also capable of providing the carrying medium to the processed *Morinda citrifolia* product. Specific carrier mediums formulations are well known in the art and not described in detail herein. The purpose of the carrier medium is as stated, to provide a means to embody the processed *Morinda citrifolia* product within the internal composition that is capable of being introduced into the body, and particularly, into the colon region.

The following examples set forth and present the effects of *Morinda citrifolia* on cancerous cells within the region of the colon, as well as the preventative and treatment effects of *Morinda citrifolia* against the proliferation or metastasizing of these cancerous cells. These examples are not intended to be limiting in any way, but are merely illustrative of the benefits and advantageous, as well as the remedial effects, of *Morinda citrifolia* on colon cancer.

EXAMPLE ONE

In a recent pharmacology laboratory test, scientists sought to evaluate the growth effects of processed *Morinda citrifolia* products on human colon tumor cell lines. It was discovered that the present invention processed *Morinda citrifolia* products feature Cyclooxygenase-1 and 2 (or Cox-1 and Cox-2) implications. Cox-1 is the constitutive and used to synthesize protective prostaglandins to line stomach and maintain normal renal function. Cox-2 is inducible and induced at infected sites by those associated with inflammation, such as bacterial polysaccharide and cytokines, interleukin-1 and 2, and tumor necrosis factor. High levels of Cox-2 are an indication of body malfunction. Therefore, it is known that Cox-1 is needed and Cox-2 is desirably inhibited.

It has been found by the scientific study conducted herein that colon cancer tumors or cells express or present high levels of Cox-2, but a normal level of Cox-1. Moreover, it was discovered that an increase in prostaglandins decreases the apoptotic (natural death) rate of cancer cells, an undesirable consequence. The apoptotic rate is restored to normal by inhibition of prostaglandin production. And, since prostaglandins are synthesized mainly by Cox-2, the inhibition of Cox-2 therefore results in a higher rate of apoptosis of cancer cells. As such, the present invention processed *Morinda citrifolia* products were tested for their ability to inhibit Cox-2, which therefore decreases prostaglandin production and increases apoptosis.

A colon tumor assay was used to detect changes in cell proliferation based on the ability of viable cells to cause alamarBlue to change from its oxidized state (non-fluorescent, blue) to a reduced (fluorescent, red) form. With the results obtained from the alamarBlue reaction, cell proliferation can be quantified and metabolic activity of viable cells can be examined. MDA-1 (a processed *Morinda citrifolia* product) was tested for its effect upon the proliferation of human colon tumor cell line (or DLD-1), and at five final assay concentrations from 10% to 0.5% through 2-fold serial dilutions.

Based on the results obtained, *Morinda citrifolia* exhibited significant growth inhibition (>50%) relative to the respective vehicle treated control group at concentration between 10% and 2% in human colon tumor cell line of DLD-1 (see Table 1-1).

Significant activity was observed for the concurrently tested standard reference agent Mitomycin at <10 μM (see Table 1–2). Consequently, semi-quantitative determinations of estimated $IC_{50}$ (50% inhibition concentration), TGI (total growth inhibition), and $LC_{50}$ (50% lethal concentration) by nonlinear regression analysis were calculated (see Table 2).

The MDA-1 test compound, or *Morinda citrifolia* fruit juice, was used for in vitro anti-tumor studies. The test compound was in liquid form and diluted with phosphate-buffered saline to obtain initial working solutions. In testing, 100-fold dilution was made in culture media to get final assay concentrations of 10%, 5%, 2%, 1%, and 0.5%.

The human colon tumor cell line of DLD-1 was obtained from American Type Culture Collection (ATCC CCL-221). The culture was used with RPMI 1640, 90%; Fetal Bovine Serum, 10% and supplemented with 1% Antibiotic-Antimycotic and the cells were incubated in an atmosphere containing 5% $CO_2$ at 37 degrees Celsius.

In the evaluation of anti-proliferation for test substances, aliquots of 100 μL of cell suspension.

In the determination of $IC_{50}$, TGI and $LC_{50}$, the measured results were calculated by the following formula:

$$PG(\%) = 100 \times (\text{Mean } F_{test} - \text{Mean } F_{time0})/(\text{Mean } F_{ctrl} - \text{Mean } F_{time0})$$

If $(\text{Mean } F_{test} - \text{Mean } F_{time0}) < 0$, then $$PG(\%) = 100 \times (\text{Mean } F_{test} - \text{Mean } F_{time0})/(\text{Mean } F_{time0} - \text{Mean } F_{blank})$$

Where:
PG: percent growth
Mean $F_{time0}$=The average of two measured fluorescent intensities of reduced alamarBlue at the time just before exposure of cells to the test substance.
Mean $F_{test}$=The average of two measured fluorescent intensities of alamarBlue after seventy-two hour exposure of cells to the test substance.
Mean $F_{ctrl}$=The average of two measured fluorescent intensities of alamarBlue after seventy-two hour incubation without the test substance.
Mean $F_{blank}$=The average of two measured fluorescent intensities of alamarBlue in medium without cells after seventy-two hour incubation.

A decrease of fifty percent or more ($\geq 50\%$) in fluorescent intensity relative to vehicle-treated control indicated significant cell growth inhibition, cytostatic or cytotoxic activity, and a semi-quantitative $IC_{50}$, TGI and $LC_{50}$ were then determined by nonlinear regression using GraphPad Prism (GraphPad Software, USA).

$IC_{50}$ (50% Inhibition Concentration): Test compound concentration where the increase from $time_0$ in the number or mass of treated cells was only 50% as much as the corresponding increase in the vehicle-control at the end of experiment.

TGI (Total Growth Inhibition): Test compound concentration where the number or mass of treated cells at the end of experiment was equal to that at $time_0$.

$LC_{50}$ (50% Lethal concentration): Test compound concentration where the number or mass of treated cells at the end of experiment was half that at $time_0$.

TABLE 1-1

The Cell Percent Growth in Variable Concentrations of Test Compound

Percent Growth (Mean ± SEM, n = 2)

| Treatment | Assay Name | Blank | Time$_0$ | Vehicle | Concentration | | | | |
|---|---|---|---|---|---|---|---|---|---|
| | | | | | 10% | 5% | 2% | 1% | 0.5% |
| PT# 1010069-ADD (MDA-1) (Tahitian Noni Juice) | 370200 Colon, DLD-1 | −100 | 0 | 100 | −56 ± 6 | 29 ± 5 | 93 ± 1 | 99 ± 6 | 98 ± 2 |

TABLE 1-2

The Cell Percent Growth in Variable Concentrations of Mitomycin

Percent Growth (Mean ± SEM, n = 2)

| Treatment | Assay Name | Blank | Time$_0$ | Vehicle | Concentration (μM) | | | | |
|---|---|---|---|---|---|---|---|---|---|
| | | | | | 10 | 1 | 0.1 | 0.01 | 0.001 |
| Mitomycin | 370200 Colon, DLD-1 | −100 | 0 | 100 | −50 ± 8 | 35 ± 4 | 60 ± 7 | 103 ± 6 | 95 ± 5 |

A decrease of 50% or more ($\geq 50\%$) in fluorescent intensity relative to vehicle-treated control indicated significant growth inhibition, cytostatic or cytotoxic activity.

TABLE 2

The Estimated IC$_{50}$, TGI and LC$_{50}$

| Treatment | Prot. # | Assay Name | $^a$IC$_{50}$ | $^b$TGI | $^c$LC$_{50}$ |
|---|---|---|---|---|---|
| PT# 1010069-ADD (MDA-1) (Tahitian Noni Juice) | 370200 | Tumor, Colon, DLD-1 | 4.2% | 6.3% | 9.4% |
| Mitomycin | 370200 | Tumor, Colon, DLD-1 | 0.38 µM | 2.2 µM | >10 µM |

$^a$IC$_{50}$ (50% Inhibition Concentration): Test compound concentration where the increase from time$_0$ in the number or mass of treated cells was only 50% as much as the corresponding increase in the vehicle-control at the end of experiment.
$^b$TGI (Total Growth Inhibition): Test compound concentration where the number or mass of treated cells at the end of experiment was equal to that at time$_0$.
$^c$LC$_{50}$ (50% Lethal Concentration): Test compound concentration where the number or mass of treated cells at the end of experiment was half that at time$_0$.

A semi-quantitative determination of IC$_{50}$, TGI and LC$_{50}$ was carried out by nonlinear regression analysis using GraphPad Prism (GraphPad Software, USA).

The following experiment shows the following:
a) IC$_{50}$ (50% Growth Inhibition Concentration) was 4.2%;
b) TGI (Total Growth Inhibition) was 6.3%; and
c) LC$_{50}$ (50% Lethal Concentration) was 9.4%.

Based on the foregoing, it can be concluded that the processed *Morinda citrifolia* products of the present invention inhibit the growth cancerous cells within the colon.

The present invention may be embodied in other specific forms without departing from its spirit of essential characteristics. The described embodiments are to be considered in all respects only al illustrative and not restrictive. The scope of the invention is, therefore, indicated by the appended claims, rather than by the foregoing description. All changes which come within the meaning and range of equivalency of the claims are to be embraced within their scope.

The invention claimed is:

1. A method for decreasing the proliferation of human colon adenocarcinoma cells, said method comprising:
   introducing to said human colon adenocarcinoma cells a composition comprising a processed *Morinda citrifolia* product present in an amount between about 0.01 and 100 percent by weight of the composition, said processed *Morinda citrifolia* product comprising the active ingredient Quercetin, wherein said processed *Morinda citrifolia* product is selected from the group consisting of *Morinda citrifolia* fruit juice, *Morinda citrifolia* puree juice, *Morinda citrifolia* puree, *Morinda citrifolia* fruit juice concentrate and *Morinda citrifolia* puree juice concentrate.

2. The method of claim 1, wherein said Quercetin is present in an amount between about 0.1 and 10 percent by weight.

3. The method of claim 1, wherein said processed *Morinda citrifolia* product further comprises Rutin.

4. The method of claim 3, wherein said Rutin is present in an amount between about 0.1 and 10 percent by weight of the composition.

5. The method of claim 1, wherein said composition is administered orally.

6. The method of claim 1, wherein said composition is administered transdermally to said adenocarcinoma cells.

7. The method of claim 1, wherein said composition is administered by injection into said adenocarcinoma cells.

8. The method of claim 1, wherein said composition is administered intravenously.

9. The method of claim 1, wherein said composition is administered systemically.

\* \* \* \* \*